United States Patent
Kim

(10) Patent No.: US 11,312,947 B2
(45) Date of Patent: Apr. 26, 2022

(54) RECOMBINANT PETASE PRODUCING STRAIN, RECOMBINANT MHETASE PRODUCING STRAIN, AND COMPOSITION FOR DEGRADING PET CONTAINING THE SAME

(71) Applicant: Kyungpook National University Industry-Academic Cooperation Foundation, Daegu (KR)

(72) Inventor: Kyung Jin Kim, Daegu (KR)

(73) Assignee: KYUNGPOOK NATIONAL UNIVERSITY INDUSTRY-ACADEMIC COOPERATION FOUNDATION, Daegu (KR)

( * ) Notice: Subject to any disclaimer, the term of this patent is extended or adjusted under 35 U.S.C. 154(b) by 101 days.

(21) Appl. No.: 16/700,165

(22) Filed: Dec. 2, 2019

(65) Prior Publication Data

US 2020/0216851 A1 Jul. 9, 2020

(30) Foreign Application Priority Data

Dec. 4, 2018 (KR) .................. 10-2018-0154759

(51) Int. Cl.
| | |
|---|---|
| *C12N 9/18* | (2006.01) |
| *C12N 1/20* | (2006.01) |
| *C12N 15/00* | (2006.01) |
| *C12N 15/62* | (2006.01) |
| *C12N 15/70* | (2006.01) |
| *C07K 14/245* | (2006.01) |

(52) U.S. Cl.
CPC .............. *C12N 9/18* (2013.01); *C12N 15/625* (2013.01); *C12N 15/70* (2013.01); *C07K 14/245* (2013.01); *C07K 2319/02* (2013.01)

(58) Field of Classification Search
CPC ................................ C12N 9/18; C12N 15/625
See application file for complete search history.

(56) References Cited

U.S. PATENT DOCUMENTS

2021/0180007 A1* 6/2021 Beckham ................. C12N 1/20

OTHER PUBLICATIONS

Choi. Secretory and extracellular production of recombinant proteins using *Escherichia coli*. Appl Microbiol Biotechnol . Jun. 2004;64(5):625-35. Epub Feb. 14, 2004.*
Joo. Structural insight into molecular mechanism of poly(ethylene terephthalate) degradation. Nat Commun. Jan. 26, 2018;9(1):382.*
(Continued)

*Primary Examiner* — Yong D Pak
(74) *Attorney, Agent, or Firm* — Wenderoth, Lind & Ponack, L.L.P.

(57) ABSTRACT

Disclosed are a recombinant poly(ethylene terephthalate) hydrolase (PETase) expression vector, a recombinant mono (2-hydroxyethyl)terephthalate hydrolase (MHETase) expression vector, a strain for producing each of the recombinant PETase and MHETase containing each of the vectors, and a method for degrading a plastics using each of the recombinant PETase and MHETase expressed therefrom. When the recombinant hydrolases, that is, PETase and MHETase are used together, high enzymatic activity may be sustained for a long time to completely degrade the PET.

4 Claims, 8 Drawing Sheets

Specification includes a Sequence Listing.

(56) References Cited

OTHER PUBLICATIONS

Yoshida et al., "A bacterium that degrades and assimilates poly(ethylene terephthalate)", Science 351(6278):1196-1199 (2016).
Han et al., "Structural insight into catalytic mechanism of PET hydrolase", Nature Communications, 8(2106): 1-6 (2017).
Seo et al., "Production of extracellular PETase from *Ideonella sakaiensis* using sec-dependent signal peptides in *E. coli*", Biochemical and Biophysical Research Communications, 508: 250-255 (2019).

* cited by examiner

SEQUENCE LISTING

```
<160> NUMBER OF SEQ ID NOS: 49

<210> SEQ ID NO 1
<211> LENGTH: 26
<212> TYPE: PRT
<213> ORGANISM: Artificial Sequence
<220> FEATURE:
<223> OTHER INFORMATION: maltose/maltodextrin binding periplasmic
      protein (SPMalE)

<400> SEQUENCE: 1

Met Lys Ile Lys Thr Gly Ala Arg Ile Leu Ala Leu Ser Ala Leu Thr
1               5                   10                  15

Thr Met Met Phe Ser Ala Ser Ala Leu Ala
            20                  25

<210> SEQ ID NO 2
<211> LENGTH: 15
<212> TYPE: PRT
<213> ORGANISM: Artificial Sequence
<220> FEATURE:
<223> OTHER INFORMATION: maltoporin (SPLamB)

<400> SEQUENCE: 2

Met Met Ile Thr Leu Arg Lys Leu Pro Leu Ala Val Ala Val Ala
```

<210> SEQ ID NO 3
<211> LENGTH: 20
<212> TYPE: PRT
<213> ORGANISM: Artificial Sequence
<220> FEATURE:
<223> OTHER INFORMATION: periplasmic molecular chaperone SurA (SPSurA)

<400> SEQUENCE: 3

```
Met Lys Asn Trp Lys Thr Leu Leu Leu Gly Ile Ala Met Ile Ala Asn
 1               5                  10                  15

Thr Ser Phe Ala
            20
```

<210> SEQ ID NO 4
<211> LENGTH: 19
<212> TYPE: PRT
<213> ORGANISM: Artificial Sequence
<220> FEATURE:
<223> OTHER INFORMATION: thiol:disulfide interchange protein DsbA
      (SPDsbA)

<400> SEQUENCE: 4

```
Met Lys Lys Ile Trp Leu Ala Leu Ala Gly Leu Val Leu Ala Phe Ser
 1               5                  10                  15

Ala Ser Ala
```

<210> SEQ ID NO 5
<211> LENGTH: 21
<212> TYPE: PRT
<213> ORGANISM: Artificial Sequence
<220> FEATURE:
<223> OTHER INFORMATION: Tol-Pal system protein TolB (SPTolB)

<400> SEQUENCE: 5

```
Met Lys Gln Ala Leu Arg Val Ala Phe Gly Phe Leu Ile Leu Trp Ala
 1               5                  10                  15

Ser Val Leu His Ala
            20
```

<210> SEQ ID NO 6
<211> LENGTH: 257
<212> TYPE: PRT
<213> ORGANISM: Artificial Sequence
<220> FEATURE:
<223> OTHER INFORMATION: PET hydrolase (IsPETase)

<400> SEQUENCE: 6

```
Arg Gly Pro Asn Pro Thr Ala Ala Ser Leu Glu Ala Ser Ala Gly Pro
 1               5                  10                  15

Phe Thr Val Arg Ser Phe Thr Val Ser Arg Pro Ser Gly Tyr Gly Ala
                20                  25                  30

Gly Thr Val Tyr Tyr Pro Thr Asn Ala Gly Gly Thr Val Gly Ala Ile
            35                  40                  45

Ala Ile Val Pro Gly Tyr Thr Ala Arg Gln Ser Ser Ile Lys Trp Trp
        50                  55                  60

Gly Pro Arg Leu Ala Ser His Gly Phe Val Val Ile Thr Ile Asp Thr
 65                  70                  75                  80

Asn Ser Thr Leu Asp Gln Pro Ser Ser Arg Ser Ser Gln Gln Met Ala
                85                  90                  95

Ala Leu Arg Gln Val Ala Ser Leu Asn Gly Thr Ser Ser Ser Pro Ile
```

```
            100                 105                 110
Tyr Gly Lys Val Asp Thr Ala Arg Met Gly Val Met Gly Trp Ser Met
            115                 120                 125
Gly Gly Gly Gly Ser Leu Ile Ser Ala Ala Asn Asn Pro Ser Leu Lys
            130                 135                 140
Ala Ala Ala Pro Gln Ala Pro Trp Asp Ser Ser Thr Asn Phe Ser Ser
145                 150                 155                 160
Val Thr Val Pro Thr Leu Ile Phe Ala Cys Glu Asn Asp Ser Ile Ala
                    165                 170                 175
Pro Val Asn Ser Ser Ala Leu Pro Ile Tyr Asp Ser Met Ser Arg Asn
                    180                 185                 190
Ala Lys Gln Phe Leu Glu Ile Asn Gly Gly Ser His Ser Cys Ala Asn
            195                 200                 205
Ser Gly Asn Ser Asn Gln Ala Leu Ile Gly Lys Lys Gly Val Ala Trp
            210                 215                 220
Met Lys Arg Phe Met Asp Asn Asp Thr Arg Tyr Ser Thr Phe Ala Cys
225                 230                 235                 240
Glu Asn Pro Asn Ser Thr Arg Val Ser Asp Phe Arg Thr Ala Asn Cys
                    245                 250                 255
Ser

<210> SEQ ID NO 7
<211> LENGTH: 586
<212> TYPE: PRT
<213> ORGANISM: Artificial Sequence
<220> FEATURE:
<223> OTHER INFORMATION: MHET hydrolase (IsMHETase)

<400> SEQUENCE: 7

Cys Ala Gly Gly Gly Ser Thr Pro Leu Pro Leu Pro Gln Gln Gln Pro
1               5                   10                  15
Pro Gln Gln Glu Pro Pro Pro Pro Val Pro Leu Ala Ser Arg Ala
            20                  25                  30
Ala Cys Glu Ala Leu Lys Asp Gly Asn Gly Asp Met Val Trp Pro Asn
            35                  40                  45
Ala Ala Thr Val Val Glu Val Ala Ala Trp Arg Asp Ala Ala Pro Ala
50                  55                  60
Thr Ala Ser Ala Ala Ala Leu Pro Glu His Cys Glu Val Ser Gly Ala
65                  70                  75                  80
Ile Ala Lys Arg Thr Gly Ile Asp Gly Tyr Pro Tyr Glu Ile Lys Phe
                85                  90                  95
Arg Leu Arg Met Pro Ala Glu Trp Asn Gly Arg Phe Phe Met Glu Gly
            100                 105                 110
Gly Ser Gly Thr Asn Gly Ser Leu Ser Ala Ala Thr Gly Ser Ile Gly
            115                 120                 125
Gly Gly Gln Ile Ala Ser Ala Leu Ser Arg Asn Phe Ala Thr Ile Ala
            130                 135                 140
Thr Asp Gly Gly His Asp Asn Ala Val Asn Asp Asn Pro Asp Ala Leu
145                 150                 155                 160
Gly Thr Val Ala Phe Gly Leu Asp Pro Gln Ala Arg Leu Asp Met Gly
                    165                 170                 175
Tyr Asn Ser Tyr Asp Gln Val Thr Gln Ala Gly Lys Ala Ala Val Ala
                    180                 185                 190
Arg Phe Tyr Gly Arg Ala Ala Asp Lys Ser Tyr Phe Ile Gly Cys Ser
            195                 200                 205
```

Glu Gly Gly Arg Glu Gly Met Met Leu Ser Gln Arg Phe Pro Ser His
              210                 215                 220

Tyr Asp Gly Ile Val Ala Gly Ala Pro Gly Tyr Gln Leu Pro Lys Ala
225                 230                 235                 240

Gly Ile Ser Gly Ala Trp Thr Thr Gln Ser Leu Ala Pro Ala Ala Val
                245                 250                 255

Gly Leu Asp Ala Gln Gly Val Pro Leu Ile Asn Lys Ser Phe Ser Asp
            260                 265                 270

Ala Asp Leu His Leu Leu Ser Gln Ala Ile Leu Gly Thr Cys Asp Ala
        275                 280                 285

Leu Asp Gly Leu Ala Asp Gly Ile Val Asp Asn Tyr Arg Ala Cys Gln
    290                 295                 300

Ala Ala Phe Asp Pro Ala Thr Ala Ala Asn Pro Ala Asn Gly Gln Ala
305                 310                 315                 320

Leu Gln Cys Val Gly Ala Lys Thr Ala Asp Cys Leu Ser Pro Val Gln
                325                 330                 335

Val Thr Ala Ile Lys Arg Ala Met Ala Gly Pro Val Asn Ser Ala Gly
            340                 345                 350

Thr Pro Leu Tyr Asn Arg Trp Ala Trp Asp Ala Gly Met Ser Gly Leu
        355                 360                 365

Ser Gly Thr Thr Tyr Asn Gln Gly Trp Arg Ser Trp Trp Leu Gly Ser
    370                 375                 380

Phe Asn Ser Ser Ala Asn Asn Ala Gln Arg Val Ser Gly Phe Ser Ala
385                 390                 395                 400

Arg Ser Trp Leu Val Asp Phe Ala Thr Pro Pro Glu Pro Met Pro Met
                405                 410                 415

Thr Gln Val Ala Ala Arg Met Met Lys Phe Asp Phe Asp Ile Asp Pro
            420                 425                 430

Leu Lys Ile Trp Ala Thr Ser Gly Gln Phe Thr Gln Ser Ser Met Asp
        435                 440                 445

Trp His Gly Ala Thr Ser Thr Asp Leu Ala Ala Phe Arg Asp Arg Gly
    450                 455                 460

Gly Lys Met Ile Leu Tyr His Gly Met Ser Asp Ala Ala Phe Ser Ala
465                 470                 475                 480

Leu Asp Thr Ala Asp Tyr Tyr Glu Arg Leu Gly Ala Ala Met Pro Gly
                485                 490                 495

Ala Ala Gly Phe Ala Arg Leu Phe Leu Val Pro Gly Met Asn His Cys
            500                 505                 510

Ser Gly Gly Pro Gly Thr Asp Arg Phe Asp Met Leu Thr Pro Leu Val
        515                 520                 525

Ala Trp Val Glu Arg Gly Glu Ala Pro Asp Gln Ile Ser Ala Trp Ser
    530                 535                 540

Gly Thr Pro Gly Tyr Phe Gly Val Ala Ala Arg Thr Arg Pro Leu Cys
545                 550                 555                 560

Pro Tyr Pro Gln Ile Ala Arg Tyr Lys Gly Ser Gly Asp Ile Asn Thr
                565                 570                 575

Glu Ala Asn Phe Ala Cys Ala Ala Pro Pro
            580                 585

<210> SEQ ID NO 8
<211> LENGTH: 270
<212> TYPE: PRT
<213> ORGANISM: Artificial Sequence
<220> FEATURE:

<223> OTHER INFORMATION: protein chaperone FkpA

<400> SEQUENCE: 8

```
Met Lys Ser Leu Phe Lys Val Thr Leu Leu Ala Thr Met Ala Val
1               5                   10                  15

Ala Leu His Ala Pro Ile Thr Phe Ala Ala Glu Ala Lys Pro Ala
            20                  25                  30

Thr Ala Ala Asp Ser Lys Ala Ala Phe Lys Asn Asp Asp Gln Lys Ser
            35                  40                      45

Ala Tyr Ala Leu Gly Ala Ser Leu Gly Arg Tyr Met Glu Asn Ser Leu
    50                  55                  60

Lys Glu Gln Glu Lys Leu Gly Ile Lys Leu Asp Lys Asp Gln Leu Ile
65                  70                  75                  80

Ala Gly Val Gln Asp Ala Phe Ala Asp Lys Ser Lys Leu Ser Asp Gln
                85                  90                  95

Glu Ile Glu Gln Thr Leu Gln Ala Phe Glu Ala Arg Val Lys Ser Ser
            100                 105                 110

Ala Gln Ala Lys Met Glu Lys Asp Ala Ala Asp Asn Glu Ala Lys Gly
        115                 120                 125

Lys Glu Tyr Arg Glu Lys Phe Ala Lys Glu Lys Gly Val Lys Thr Ser
130                 135                 140

Ser Thr Gly Leu Val Tyr Gln Val Val Glu Ala Gly Lys Gly Glu Ala
145                 150                 155                 160

Pro Lys Asp Ser Asp Thr Val Val Val Asn Tyr Lys Gly Thr Leu Ile
                165                 170                 175

Asp Gly Lys Glu Phe Asp Asn Ser Tyr Thr Arg Gly Glu Pro Leu Ser
            180                 185                 190

Phe Arg Leu Asp Gly Val Ile Pro Gly Trp Thr Glu Gly Leu Lys Asn
        195                 200                 205

Ile Lys Lys Gly Gly Lys Ile Lys Leu Val Ile Pro Pro Glu Leu Ala
    210                 215                 220

Tyr Gly Lys Ala Gly Val Pro Gly Ile Pro Pro Asn Ser Thr Leu Val
225                 230                 235                 240

Phe Asp Val Glu Leu Leu Asp Val Lys Pro Ala Pro Lys Ala Asp Ala
                245                 250                 255

Lys Pro Glu Ala Asp Ala Lys Ala Ala Asp Ser Ala Lys Lys
            260                 265                 270
```

<210> SEQ ID NO 9
<211> LENGTH: 208
<212> TYPE: PRT
<213> ORGANISM: Artificial Sequence
<220> FEATURE:
<223> OTHER INFORMATION: protein chaperone DsbA

<400> SEQUENCE: 9

```
Met Lys Lys Ile Trp Leu Ala Leu Ala Gly Leu Val Leu Ala Phe Ser
1               5                   10                  15

Ala Ser Ala Ala Gln Tyr Glu Asp Gly Lys Gln Tyr Thr Thr Leu Glu
            20                  25                  30

Lys Pro Val Ala Gly Ala Pro Gln Val Leu Glu Phe Phe Ser Phe Phe
        35                  40                  45

Cys Pro His Cys Tyr Gln Phe Glu Glu Val Leu His Ile Ser Asp Asn
    50                  55                  60

Val Lys Lys Lys Leu Pro Glu Gly Val Lys Met Thr Lys Tyr His Val
65                  70                  75                  80
```

Asn Phe Met Gly Gly Asp Leu Gly Lys Asp Leu Thr Gln Ala Trp Ala
                85                  90                  95

Val Ala Met Ala Leu Gly Val Glu Asp Lys Val Thr Val Pro Leu Phe
            100                 105                 110

Glu Gly Val Gln Lys Thr Gln Thr Ile Arg Ser Ala Ser Asp Ile Arg
            115                 120                 125

Asp Val Phe Ile Asn Ala Gly Ile Lys Gly Glu Glu Tyr Asp Ala Ala
            130                 135                 140

Trp Asn Ser Phe Val Val Lys Ser Leu Val Ala Gln Gln Glu Lys Ala
145                 150                 155                 160

Ala Ala Asp Val Gln Leu Arg Gly Val Pro Ala Met Phe Val Asn Gly
                165                 170                 175

Lys Tyr Gln Leu Asn Pro Gln Gly Met Asp Thr Ser Asn Met Asp Val
            180                 185                 190

Phe Val Gln Gln Tyr Ala Asp Thr Val Lys Tyr Leu Ser Glu Lys Lys
            195                 200                 205

<210> SEQ ID NO 10
<211> LENGTH: 236
<212> TYPE: PRT
<213> ORGANISM: Artificial Sequence
<220> FEATURE:
<223> OTHER INFORMATION: protein chaperone DsbC

<400> SEQUENCE: 10

Met Lys Lys Gly Phe Met Leu Phe Thr Leu Leu Ala Ala Phe Ser Gly
1               5                   10                  15

Phe Ala Gln Ala Asp Asp Ala Ala Ile Gln Gln Thr Leu Ala Lys Met
            20                  25                  30

Gly Ile Lys Ser Ser Asp Ile Gln Pro Ala Pro Val Ala Gly Met Lys
        35                  40                  45

Thr Val Leu Thr Asn Ser Gly Val Leu Tyr Ile Thr Asp Asp Gly Lys
    50                  55                  60

His Ile Ile Gln Gly Pro Met Tyr Asp Val Ser Gly Thr Ala Pro Val
65                  70                  75                  80

Asn Val Thr Asn Lys Met Leu Leu Lys Gln Leu Asn Ala Leu Glu Lys
                85                  90                  95

Glu Met Ile Val Tyr Lys Ala Pro Gln Glu Lys His Val Ile Thr Val
            100                 105                 110

Phe Thr Asp Ile Thr Cys Gly Tyr Cys His Lys Leu His Glu Gln Met
            115                 120                 125

Ala Asp Tyr Asn Ala Leu Gly Ile Thr Val Arg Tyr Leu Ala Phe Pro
            130                 135                 140

Arg Gln Gly Leu Asp Ser Asp Ala Glu Lys Met Lys Ala Ile Trp
145                 150                 155                 160

Cys Ala Lys Asp Lys Asn Lys Ala Phe Asp Asp Val Met Ala Gly Lys
                165                 170                 175

Ser Val Ala Pro Ala Ser Cys Asp Val Asp Ile Ala Asp His Tyr Ala
            180                 185                 190

Leu Gly Val Gln Leu Gly Val Ser Gly Thr Pro Ala Val Val Leu Ser
            195                 200                 205

Asn Gly Thr Leu Val Pro Gly Tyr Gln Pro Pro Lys Glu Met Lys Glu
            210                 215                 220

Phe Leu Asp Glu His Gln Lys Met Thr Ser Gly Lys
225                 230                 235

<210> SEQ ID NO 11
<211> LENGTH: 324
<212> TYPE: PRT
<213> ORGANISM: Artificial Sequence
<220> FEATURE:
<223> OTHER INFORMATION: protein chaperone SPaseI

<400> SEQUENCE: 11

```
Met Ala Asn Met Phe Ala Leu Ile Leu Val Ile Ala Thr Leu Val Thr
 1               5                  10                  15

Gly Ile Leu Trp Cys Val Asp Lys Phe Phe Phe Ala Pro Lys Arg Arg
            20                  25                  30

Glu Arg Gln Ala Ala Ala Gln Ala Ala Ala Gly Asp Ser Leu Asp Lys
        35                  40                  45

Ala Thr Leu Lys Lys Val Ala Pro Lys Pro Gly Trp Leu Glu Thr Gly
    50                  55                  60

Ala Ser Val Phe Pro Val Leu Ala Ile Val Leu Ile Val Arg Ser Phe
65                  70                  75                  80

Ile Tyr Glu Pro Phe Gln Ile Pro Ser Gly Ser Met Met Pro Thr Leu
                85                  90                  95

Leu Ile Gly Asp Phe Ile Leu Val Glu Lys Phe Ala Tyr Gly Ile Lys
            100                 105                 110

Asp Pro Ile Tyr Gln Lys Thr Leu Ile Glu Thr Gly His Pro Lys Arg
        115                 120                 125

Gly Asp Ile Val Val Phe Lys Tyr Pro Glu Asp Pro Lys Leu Asp Tyr
    130                 135                 140

Ile Lys Arg Ala Val Gly Leu Pro Gly Asp Lys Val Thr Tyr Asp Pro
145                 150                 155                 160

Val Ser Lys Glu Leu Thr Ile Gln Pro Gly Cys Ser Ser Gly Gln Ala
                165                 170                 175

Cys Glu Asn Ala Leu Pro Val Thr Tyr Ser Asn Val Glu Pro Ser Asp
            180                 185                 190

Phe Val Gln Thr Phe Ser Arg Arg Asn Gly Gly Glu Ala Thr Ser Gly
        195                 200                 205

Phe Phe Glu Val Pro Lys Asn Glu Thr Lys Glu Asn Gly Ile Arg Leu
    210                 215                 220

Ser Glu Arg Lys Glu Thr Leu Gly Asp Val Thr His Arg Ile Leu Thr
225                 230                 235                 240

Val Pro Ile Ala Gln Asp Gln Val Gly Met Tyr Tyr Gln Gln Pro Gly
                245                 250                 255

Gln Gln Leu Ala Thr Trp Ile Val Pro Pro Gly Gln Tyr Phe Met Met
            260                 265                 270

Gly Asp Asn Arg Asp Asn Ser Ala Asp Ser Arg Tyr Trp Gly Phe Val
        275                 280                 285

Pro Glu Ala Asn Leu Val Gly Arg Ala Thr Ala Ile Trp Met Ser Phe
    290                 295                 300

Asp Lys Gln Glu Gly Glu Trp Pro Thr Gly Leu Arg Leu Ser Arg Ile
305                 310                 315                 320

Gly Gly Ile His
```

<210> SEQ ID NO 12
<211> LENGTH: 155
<212> TYPE: PRT
<213> ORGANISM: Artificial Sequence
<220> FEATURE:

<223> OTHER INFORMATION: protein chaperone SecB

<400> SEQUENCE: 12

Met Ser Glu Gln Asn Thr Glu Met Thr Phe Gln Ile Gln Arg Ile
1               5                   10                  15

Tyr Thr Lys Asp Ile Ser Phe Glu Ala Pro Asn Ala Pro His Val Phe
            20                  25                  30

Gln Lys Asp Trp Gln Pro Glu Val Lys Leu Asp Leu Asp Thr Ala Ser
        35                  40                  45

Ser Gln Leu Ala Asp Asp Val Tyr Glu Val Val Leu Arg Val Thr Val
    50                  55                  60

Thr Ala Ser Leu Gly Glu Glu Thr Ala Phe Leu Cys Glu Val Gln Gln
65                  70                  75                  80

Gly Gly Ile Phe Ser Ile Ala Gly Ile Glu Gly Thr Gln Met Ala His
                85                  90                  95

Cys Leu Gly Ala Tyr Cys Pro Asn Ile Leu Phe Pro Tyr Ala Arg Glu
            100                 105                 110

Cys Ile Thr Ser Met Val Ser Arg Gly Thr Phe Pro Gln Leu Asn Leu
        115                 120                 125

Ala Pro Val Asn Phe Asp Ala Leu Phe Met Asn Tyr Leu Gln Gln Gln
    130                 135                 140

Ala Gly Glu Gly Thr Glu Glu His Gln Asp Ala
145                 150                 155

<210> SEQ ID NO 13
<211> LENGTH: 34
<212> TYPE: DNA
<213> ORGANISM: Artificial Sequence
<220> FEATURE:
<223> OTHER INFORMATION: chemically-synthesized PCR primer

<400> SEQUENCE: 13
gcgcccatgg cgcgcggtcc gaatccgaca gccg        34

<210> SEQ ID NO 14
<211> LENGTH: 34
<212> TYPE: DNA
<213> ORGANISM: Artificial Sequence
<220> FEATURE:
<223> OTHER INFORMATION: chemically-synthesized PCR primer

<400> SEQUENCE: 14
gcgcctcgag gctgcaattc gctgtacgaa aatc        34

<210> SEQ ID NO 15
<211> LENGTH: 34
<212> TYPE: DNA
<213> ORGANISM: Artificial Sequence
<220> FEATURE:
<223> OTHER INFORMATION: chemically-synthesized PCR primer

<400> SEQUENCE: 15
gcgccatatg aaaataaaaa caggtgcacg catc        34

<210> SEQ ID NO 16
<211> LENGTH: 34
<212> TYPE: DNA
<213> ORGANISM: Artificial Sequence
<220> FEATURE:
<223> OTHER INFORMATION: chemically-synthesized PCR primer

<400> SEQUENCE: 16
gcgcccatgg cgagagccga ggcggaaaac atca                                34

<210> SEQ ID NO 17
<211> LENGTH: 34
<212> TYPE: DNA
<213> ORGANISM: Artificial Sequence
<220> FEATURE:
<223> OTHER INFORMATION: chemically-synthesized PCR primer

<400> SEQUENCE: 17
gcgccatatg atgattactc tgcgcaaact tcct                                34

<210> SEQ ID NO 18
<211> LENGTH: 34
<212> TYPE: DNA
<213> ORGANISM: Artificial Sequence
<220> FEATURE:
<223> OTHER INFORMATION: chemically-synthesized PCR primer

<400> SEQUENCE: 18
gcgcccatgg ccattgcctg agcagacatt acgc                                34

<210> SEQ ID NO 19
<211> LENGTH: 34
<212> TYPE: DNA
<213> ORGANISM: Artificial Sequence
<220> FEATURE:
<223> OTHER INFORMATION: chemically-synthesized PCR primer

<400> SEQUENCE: 19
gcgccatatg aagaactgga aaacgctgct tctc                                34

<210> SEQ ID NO 20
<211> LENGTH: 34
<212> TYPE: DNA
<213> ORGANISM: Artificial Sequence
<220> FEATURE:
<223> OTHER INFORMATION: chemically-synthesized PCR primer

<400> SEQUENCE: 20
gcgcccatgg cgaaactggt attcgcgatc atgg                                34

<210> SEQ ID NO 21
<211> LENGTH: 34
<212> TYPE: DNA
<213> ORGANISM: Artificial Sequence
<220> FEATURE:
<223> OTHER INFORMATION: chemically-synthesized PCR primer

<400> SEQUENCE: 21
gcgccatatg aaaaagattt ggctggcgct ggct                                34

<210> SEQ ID NO 22
<211> LENGTH: 34
<212> TYPE: DNA
<213> ORGANISM: Artificial Sequence
<220> FEATURE:
<223> OTHER INFORMATION: chemically-synthesized PCR primer

<400> SEQUENCE: 22
gcgcccatgg ccgatgcgct aaacgctaaa acta                                34

<210> SEQ ID NO 23
<211> LENGTH: 34
<212> TYPE: DNA

<213> ORGANISM: Artificial Sequence
<220> FEATURE:
<223> OTHER INFORMATION: chemically-synthesized PCR primer

<400> SEQUENCE: 23
gcgccatatg aagcaggcat tacgagtagc attt          34

<210> SEQ ID NO 24
<211> LENGTH: 34
<212> TYPE: DNA
<213> ORGANISM: Artificial Sequence
<220> FEATURE:
<223> OTHER INFORMATION: chemically-synthesized PCR primer

<400> SEQUENCE: 24
gcgcccatgg catgcagaac tgatgcccac agta          34

<210> SEQ ID NO 25
<211> LENGTH: 34
<212> TYPE: DNA
<213> ORGANISM: Artificial Sequence
<220> FEATURE:
<223> OTHER INFORMATION: chemically-synthesized PCR primer

<400> SEQUENCE: 25
gcgcccatgg cgtgtgctgg cggtgggtcc acgc          34

<210> SEQ ID NO 26
<211> LENGTH: 30
<212> TYPE: DNA
<213> ORGANISM: Artificial Sequence
<220> FEATURE:
<223> OTHER INFORMATION: chemically-synthesized PCR primer

<400> SEQUENCE: 26
gcgcgctcga ggggaggagc cgcgcaggcg          30

<210> SEQ ID NO 27
<211> LENGTH: 34
<212> TYPE: DNA
<213> ORGANISM: Artificial Sequence
<220> FEATURE:
<223> OTHER INFORMATION: chemically-synthesized PCR primer

<400> SEQUENCE: 27
gcgccatatg aaatcactgt ttaaagtaac gctg          34

<210> SEQ ID NO 28
<211> LENGTH: 34
<212> TYPE: DNA
<213> ORGANISM: Artificial Sequence
<220> FEATURE:
<223> OTHER INFORMATION: chemically-synthesized PCR primer

<400> SEQUENCE: 28
gcgcctcgag ttatttttta gcagaatctg cggc          34

<210> SEQ ID NO 29
<211> LENGTH: 34
<212> TYPE: DNA
<213> ORGANISM: Artificial Sequence
<220> FEATURE:
<223> OTHER INFORMATION: chemically-synthesized PCR primer

<400> SEQUENCE: 29
gcgcccatgg agaaaggttt tatgttgttt actt          34

<210> SEQ ID NO 30
<211> LENGTH: 34
<212> TYPE: DNA
<213> ORGANISM: Artificial Sequence
<220> FEATURE:
<223> OTHER INFORMATION: chemically-synthesized PCR primer

<400> SEQUENCE: 30
gcgcgcggcc gcttatttac cgctggtcat tttt         34

<210> SEQ ID NO 31
<211> LENGTH: 34
<212> TYPE: DNA
<213> ORGANISM: Artificial Sequence
<220> FEATURE:
<223> OTHER INFORMATION: chemically-synthesized PCR primer

<400> SEQUENCE: 31
gcgccatatg aaaagattt ggctggcgct ggct          34

<210> SEQ ID NO 32
<211> LENGTH: 34
<212> TYPE: DNA
<213> ORGANISM: Artificial Sequence
<220> FEATURE:
<223> OTHER INFORMATION: chemically-synthesized PCR primer

<400> SEQUENCE: 32
gcgcctcgag ttatttttc tcggacagat attt           34

<210> SEQ ID NO 33
<211> LENGTH: 34
<212> TYPE: DNA
<213> ORGANISM: Artificial Sequence
<220> FEATURE:
<223> OTHER INFORMATION: chemically-synthesized PCR primer

<400> SEQUENCE: 33
gcgcccatgg cagaacaaaa caacactgaa atga          34

<210> SEQ ID NO 34
<211> LENGTH: 34
<212> TYPE: DNA
<213> ORGANISM: Artificial Sequence
<220> FEATURE:
<223> OTHER INFORMATION: chemically-synthesized PCR primer

<400> SEQUENCE: 34
gcgcgcggcc gctcaggcat cctgatgttc ttca          34

<210> SEQ ID NO 35
<211> LENGTH: 34
<212> TYPE: DNA
<213> ORGANISM: Artificial Sequence
<220> FEATURE:
<223> OTHER INFORMATION: chemically-synthesized PCR primer

<400> SEQUENCE: 35
gcgccatatg gcgaatatgt ttgccctgat tctg          34

<210> SEQ ID NO 36
<211> LENGTH: 34
<212> TYPE: DNA
<213> ORGANISM: Artificial Sequence
<220> FEATURE:

<223> OTHER INFORMATION: chemically-synthesized PCR primer

<400> SEQUENCE: 36
gcgcctcgag ttaatggatg ccgccaatgc gact                    34

<210> SEQ ID NO 37
<211> LENGTH: 33
<212> TYPE: DNA
<213> ORGANISM: Artificial Sequence
<220> FEATURE:
<223> OTHER INFORMATION: chemically-synthesized PCR primer

<400> SEQUENCE: 37
acgttagacc agccagaaag tcggagttcg caa                     33

<210> SEQ ID NO 38
<211> LENGTH: 33
<212> TYPE: DNA
<213> ORGANISM: Artificial Sequence
<220> FEATURE:
<223> OTHER INFORMATION: chemically-synthesized PCR primer

<400> SEQUENCE: 38
ttgcgaactc cgactttctg gctggtctaa cgt                     33

<210> SEQ ID NO 39
<211> LENGTH: 33
<212> TYPE: DNA
<213> ORGANISM: Artificial Sequence
<220> FEATURE:
<223> OTHER INFORMATION: chemically-synthesized PCR primer

<400> SEQUENCE: 39
cctcaagcac catggcattc ttcgacaaat ttt                     33

<210> SEQ ID NO 40
<211> LENGTH: 33
<212> TYPE: DNA
<213> ORGANISM: Artificial Sequence
<220> FEATURE:
<223> OTHER INFORMATION: chemically-synthesized PCR primer

<400> SEQUENCE: 40
aaaatttgtc gaagaatgcc atggtgcttg agg                     33

<210> SEQ ID NO 41
<211> LENGTH: 33
<212> TYPE: DNA
<213> ORGANISM: Artificial Sequence
<220> FEATURE:
<223> OTHER INFORMATION: chemically-synthesized PCR primer

<400> SEQUENCE: 41
aacccgaata gcaccagagt gtctgatttt cgt                     33

<210> SEQ ID NO 42
<211> LENGTH: 33
<212> TYPE: DNA
<213> ORGANISM: Artificial Sequence
<220> FEATURE:
<223> OTHER INFORMATION: chemically-synthesized PCR primer

<400> SEQUENCE: 42
acgaaaatca gacactctgg tgctattcgg gtt                     33

<210> SEQ ID NO 43
<211> LENGTH: 78
<212> TYPE: DNA
<213> ORGANISM: E. coli

<400> SEQUENCE: 43
atgaaaataa aaacaggtgc acgcatcctc gcattatccg cattaacgac gatgatgttt    60
tccgcctcgg ctctcgcc                                                  78

<210> SEQ ID NO 44
<211> LENGTH: 75
<212> TYPE: DNA
<213> ORGANISM: E. coli

<400> SEQUENCE: 44
atgatgatta ctctgcgcaa acttcctctg gcggttgccg tcgcagcggg cgtaatgtct    60
gctcaggcaa tggct                                                     75

<210> SEQ ID NO 45
<211> LENGTH: 60
<212> TYPE: DNA
<213> ORGANISM: E. coli

<400> SEQUENCE: 45
atgaagaact ggaaaacgct gcttctcggt atcgccatga tcgcgaatac cagtttcgct    60

<210> SEQ ID NO 46
<211> LENGTH: 57
<212> TYPE: DNA
<213> ORGANISM: E. coli

<400> SEQUENCE: 46
atgaaaaaga tttggctggc gctggctggt ttagttttag cgtttagcgc atcggcg       57

<210> SEQ ID NO 47
<211> LENGTH: 63
<212> TYPE: DNA
<213> ORGANISM: E. coli

<400> SEQUENCE: 47
atgaagcagg cattacgagt agcatttggt tttctcatac tgtgggcatc agttctgcat    60
gct                                                                  63

<210> SEQ ID NO 48
<211> LENGTH: 66
<212> TYPE: DNA
<213> ORGANISM: E. coli

<400> SEQUENCE: 48
atgaaatacc tgctgccgac cgctgctgct ggtctgctcc tctcgctgc ccagccggcg     60 atggcc                                                               66

<210> SEQ ID NO 49
<211> LENGTH: 99
<212> TYPE: DNA
<213> ORGANISM: Artificial Sequence
<220> FEATURE:
<223> OTHER INFORMATION: sequence encoding optimized signal peptide

```
<400> SEQUENCE: 49
atgaattttc ctcgcgcttc acgactgatg caggctgccg ttcttggagg gctgatggcc    60
gttagcgcgg ccgccaccgc tcagacaaat ccctacgcc                           99
```

RECOMBINANT PETASE PRODUCING STRAIN, RECOMBINANT MHETASE PRODUCING STRAIN, AND COMPOSITION FOR DEGRADING PET CONTAINING THE SAME

SEQUENCE LISTING

A sequence listing in electronic (ASCII text file) format is filed with this application and incorporated herein by reference. The name of the ASCII text file is "2019_2066A_revised_ST25.txt"; the file was created on Nov. 2, 2021; the size of the file is 28 KB.

CROSS-REFERENCE TO RELATED APPLICATIONS

This application claims priority to and the benefit of Korean Patent Application No. 10-2018-0154759 filed in the Korean Intellectual Property Office on Dec. 4, 2018, the entire contents of which are incorporated herein by reference.

TECHNICAL FIELD

The present invention relates to recombinant PETase and recombinant MHETase expression vectors capable of degrading a plastic, a strain for producing the recombinant PETase and recombinant MHETase containing the vectors, and a method for degrading a plastic using recombinant hydrolase expressed therefrom.

BACKGROUND ART

Polyethylene ethylene terephthalate (PET) is one of the most commonly consumed plastics, and is particularly consumed for a container and fiber. For decades, use of PET plastics has increased dramatically due to low cost, lightness, high workability and bio-inertness. However, while non-degrading properties of plastics are considered a big advantage in using plastics, environmental groups, governments and the general public are very concerned about accumulation of large amounts of PET wastes in the ocean and other ecosystems. Therefore, many efforts have been made to develop eco-friendly degrading technology of PET using microorganisms. Recently, *Ideonella sakaiensis* (201-F6) as a gram-negative bacterium that may use PET as an energy and carbon source has been isolated. The bacteria degrade PET using two important hydrolases, that is, PET hydrolase (IsPETase) and MHET hydrolase (IsMHETase). IsPETase hydrolyzes PET to monomeric MHET at 30° C. IsMHETase degrades MHET into ethylene glycol and terephthalate.

Structural analysis of IsPETase shows that the enzyme exhibits higher activity on a PET film compared to other hydrolases and esterases (ester hydrolase) and uses very large hydrophobic polymers and thus has a unique action mechanism. Thus, enzymatic hydrolysis of PET using IsPETase may provide a solution to environmental pollution by plastics.

Recent studies on IsPETase have been done primarily using recombinant expression and purified enzymes. However, the recombinant expression system has serious disadvantages when applied to the degrading of PET by microorganisms, due to a high cost purification, low stability, dissolution, and yield of the recombinant enzyme. A potential way to solve this problem is to fuse the enzyme to an N-terminal signal peptide that may move a protein precursor from a cytoplasm to a periplasm and/or extracellular. The *Ideonella sakaiensis* (*I. sakaiensis*) naturally secretes these enzymes into the extracellular space because PET multimers cannot penetrate a lipid bilayer of gram-negative bacteria. Continuous secreting and producing of IsPETase by host cells in culture/fed-batch/continuous culture medium may overcome loss of activity over time of the enzyme with relatively low structural stability and denaturation temperature of 46.8° C. Further, an oxidative environment in a periplasm is known to assist in formation of disulfide bonds. Two disulfide bonds in IsPETase play an important role in folding of proteins when IsPETase is secreted into the periplasm.

*Escherichia coli* K12 as gram-negative bacterium expresses intracellular proteins into periplasm and extracellular mainly using a type II secretion mechanism. A system that expresses proteins into periplasm includes a Sec-dependent pathway, a signal recognition particle (SRP) pathway, and a twin-arginine translocation (TAT) pathway. The Sec-dependent pathway and SRP pathway may not be distinguished in vivo and involve in post-/co-translational translocation of a prefolded polypeptide passing through an endomembrane. Meanwhile, the TAT pathway secretes a folded protein.

Researchers of the present invention produced a recombinant enzyme capable of effectively degrading PET by fusing a Sec-dependent signal peptide derived from *Escherichia coli* with IsPETase and IsMHETase. Thus, a method of completely degrading PET was developed.

PRIOR ART DOCUMENTS

Non-Patent Literature (Non-patent literature 1) X. Han, W. D. Liu, J. W. Huang, J. T. Ma, Y. Y. Zheng, T. P. Ko, L. M. Xu, Y. S. Cheng, C. C. Chen, R. T. Guo. Structural insight into catalytic mechanism of PET hydrolase. Nature Communications. 13 Dec. 2017. Vol. 8.

SUMMARY OF THE INVENTION

The present invention has been made in an effort to provide expression vectors of recombinant PETase and expression vectors of recombinant MHETase that may be produced in large quantities at high yields respectively.

The present invention has also been made in an effort to provide a recombinant PETase producing strain or a recombinant MHETase producing strain containing the recombinant PETase expression vector or a recombinant MHETase expression vector respectively.

The present invention has also been made in an effort to provide a method for producing recombinant PETase or recombinant MHETase using the strain.

The present invention has also been made in an effort to provide recombinant PETase or recombinant MHETase produced by the producing method.

The present invention has also been made in an effort to provide a composition for degrading PET, the composition containing one or more strains selected from the group consisting of a recombinant PETase producing strain and a recombinant MHETase producing strain, or one or more enzyme selected from the group consisting of recombinant PETase and recombinant MHETase.

The present invention has also been made in an effort to provide a method for degrading PET using the composition.

<Recombinant PETase>

An exemplary embodiment of the present invention provides a recombinant PETase expression vector containing a polynucleotide encoding a signal peptide and a polynucleotide encoding a poly (ethylene terephthalate) hydrolase (PETase) linked to a C-terminus of the polynucleotide encoding a signal peptide.

The signal peptide (SP) is a short sequence that helps a protein synthesized in a cell to move to a correct position. The SP is usually attached to an N-terminus of the corresponding protein while having a length of 5 to 16 amino acids, and is removed therefrom when the protein moves to the correct position. The researchers of the present invention have recognized based on a previous experiment that when isPETase-encoded expression vector (pET15b) free of a leader sequence is transformed to express IsPETase, a signal peptide that could be recognized by E. coli as a transformant is required. Accordingly, in order to find an optimal signal peptide to IsPETase, the researchers performed PRED-TAT) (www.compgen.org/tools/PRED-TAT/) on IsPETase ($SP_{PETase}$) containing an existing signal peptide, a signal peptide of the Sec-dependent pathway, and a signal peptide of the TAT pathway. As a result, it is predicted that $SP_{PETase}$ is more likely to be secreted through the Sec-dependent pathway. Thus, the present invention uses a signal peptide related to the Sec-dependent pathway instead of an existing signal peptide of IsPETase.

The Sec-dependent pathway is a pathway along which a protein synthesized in a cell of gram-negative bacteria are secreted through an endomembrane to a periplasm, that is, a space between the endomembrane and extracellular membrane. The signal peptide of the Sec-dependent pathway may be maltose/maltodextrin binding periplasmic protein ($SP_{MalE}$), maltoporin ($SP_{LamB}$), periplasmic molecular chaperone SurA ($SP_{SurA}$), thiol:disulfide interchange protein DsbA ($SP_{DsbA}$), Tol-Pal system protein TolB ($SP_{TolB}$), and the like and may be selected from the group consisting of SEQ ID NOs: 1 to 5. The signal peptide in accordance with the present invention is preferably maltose/maltodextrin binding periplasmic protein ($SP_{malE}$), or maltoporin ($SP_{LamB}$). Most preferably, amino acid sequence of the signal peptide in accordance with the present invention is represented by SEQ ID NO: 1 or SEQ ID NO: 2.

The poly (ethylene terephthalate) hydrolase (PETase) is derived from *Ideonella sakaiensis* as the Gram-negative bacterium and is an enzyme that degrades PET into mono (2-hydroxyethyl)terephthalate (MHET). Amino acid sequence of such IsPETase is preferably represented by SEQ ID NO: 6 without an amino acid sequence of an existing signal peptide.

A vector in accordance with the present invention may typically be constructed as a vector for expression. In particular, a polynucleotide encoding the PETase in accordance with the present invention is derived from bacteria. In consideration of convenience of culture and the like, it is preferable to use a prokaryotic cell as a host cell. Further, this expression vector may further contain a promoter that regulates an expression of an encoded protein. The promoter may include a powerful promoter capable of advancing transcription (e.g. tac promoter, lac promoter, lacUV5 promoter, lpp promoter, pLλ promoter, pRλ promoter, racy promoter, amp promoter, recA promoter, SP6 promoter, trp promoter and T7 promoter, etc.) and may generally contain a ribosomal binding site for initiation of translation, and transcription/translation termination sequences. Further, when E. coli is used as a host cell, a promoter and an operator of a E. coli tryptophan biosynthetic pathway, a left promoter (pLλ promoter) of a phage λ, and the like may be used as a regulatory site.

In one example, the vector that may be used in the present invention may be produced by engineering a plasmid often used in the art (e.g., pSC101, ColE1, pBR322, pUC8/9, pHC79, pUC19, pET, etc.), a phage (e.g., λgt4. λB, λ-Charon, λΔz1 and M13, etc.) or viruses (e.g., SV40, etc.). However, the present invention is not limited thereto. Most preferably, pET-22b (+) which has a T7/lac promoter and thus induces a protein expression by IPTG (isopropyl β-D-1-thiogalactopyranoside) may be used.

In one example, the expression vector containing such a signal peptide and a polynucleotide encoding a PETase may be configured such that an additional sequence thereof may be linked to the C-terminus to facilitate purification of the recombinant PETase. The additional sequence that may be linked to the C-terminus may include, for example, glutathione S-transferase (Pharmacia, USA), maltose binding protein (NEB, USA), FLAG (IBI, USA) and 6×His (hexahistidine; Quiagen, USA), and the like, and, most preferably, may be 6×His. Due to the presence of the additional sequence for the purification, a protein expressed in the producing strain for producing the recombinant PETase may be easily and rapidly purified using an affinity chromatography. In one example, the expression vector in accordance with the present invention may contain, as a selection marker, antibiotic resistance genes commonly used in the art. For example, the antibiotic resistance genes may include resistance genes against ampicillin, gentamycin, carbenicillin, chloramphenicol, streptomycin, kanamycin, geneticin, neomycin, hygromycin and tetracycline.

In accordance with one exemplary embodiment, the recombinant PETase expression vector may be transformed into a host cell to obtain a transformant. The transformant is a strain capable of expressing recombinant PETase and thus is defined herein as a recombinant PETase producing strain. A host cell for obtaining the producing strain in accordance with the present invention may include a host cell as known in the art. For example, the host cell may include *E. coli* JM109, *E. coli* BL21 (DE3), *E. coli* RR1, *E. coli* LE392, *E. coli* B, *E. coli* X 1776, *E. coli* W3110, strains of genus *Bacillus* such as *Bacillus subtilis*, *Bacillus thuringiensis*, and enterobacteriaceae strains such as *Salmonella typhimurium*, *Serratia marcensons* and various *Pseudomonas* species.

A method of carrying the vector or the like into a host cell in a transformation process may include a $CaCl_2$ method (Cohen, S N et al., Proc. Natl. Acac. Sci. USA, 9: 2110-2114 (1973)), a Hanahan method (Cohen, S N et al., Proc. Natl. Acac. Sci. USA, 9: 2110-2114 (1973); and Hanahan, D., J. Mol. Biol., 166: 557-580 (1983)), and an electroporation method (Dower, W J et al., Nucleic. Acids Res., 16: 6127-6145 (1988)), etc.

The recombinant PETase producing strain may be used to produce the recombinant PETase. Specifically, the method of producing the recombinant PETase may include culturing the recombinant PETase producing strain; and obtaining a recombinant PETase from the cultured strain. A culture condition of the recombinant PETase producing strain may vary depending on a type of the transformed host cell. However, it is preferable that a temperature is 25 to 40° C., and pH is 6 to 8. The recombinant PETase produced under these conditions has excellent activity of the enzyme degrading the PET. Further, mass production thereof at a high yield may be realized.

<Recombinant MHETase>

Another exemplary embodiment provides a recombinant MHETase expression vector containing a polynucleotide encoding a signal peptide and a polynucleotide encoding mono(2-hydroxyethyl)terephthalate hydrolase (MHETase) linked to a C-terminus of the polynucleotide encoding a signal peptide.

The signal peptide may include a signal peptide related to the Sec-dependent pathway, as described in the <recombinant PETase>. The signal peptide of the Sec-dependent pathway may be maltose/maltodextrin binding periplasmic protein ($SP_{MalE}$), maltoporin ($SP_{LamB}$), periplasmic molecular chaperone SurA ($SP_{SurA}$), thiol:disulfide interchange protein DsbA ($SP_{DsbA}$), Tol-Pal system protein TolB ($SP_{TolB}$), and the like and may be selected from the group consisting of SEQ ID NOs: 1 to 5. The signal peptide in accordance with the present invention is preferably maltoporin ($SP_{LamB}$). Most preferably, amino acid sequence of the signal peptide in accordance with the present invention is represented by SEQ ID NO: 2.

The mono(2-hydroxyethyl)terephthalate hydrolase is derived from *Ideonella sakaiensis* as the gram-negative bacterium and is an enzyme that degrades MHET into ethylene glycol (EG) and terephthalate (TPA). Amino acid sequence of the IsMHETase is preferably represented by SEQ ID NO: 7 without an amino acid sequence of an existing signal peptide.

The expression vector containing the signal peptide and the polynucleotide encoding MHETase, the recombinant MHETase producing strain, and the recombinant MHETase producing method using the strain are the same as described in the <recombinant PETase> except for changing the PETase to MHETase. Thus, descriptions thereof are omitted to avoid excessive duplication of the specification. In one example, unlike the recombinant PETase producing strain, the recombinant MHETase producing strain may further contain a chaperone expression vector as well as the recombinant MHETase expression vector.

Chaperone is a protein involved in a folding or unfolding of proteins in cells. The chaperone functions to form and maintain a protein structure so that a tertiary structure of the protein does not unfold or folds in an incorrect manner. Therefore, in accordance with the present invention, chaperone is used to increase a yield of the recombinant MHETase. According to an embodiment of the present invention, the chaperone may be selected from the group consisting of FkpA, DsbA, DsbC, SPaseI and SecB, and may be selected from the group consisting of SEQ ID NOs: 8 to 12. In this connection, SEQ ID NO: 10 is preferable.

<Composition for Degrading PET and Method for Degrading PET>

The recombinant PETase and recombinant MHETase are hydrolases that can completely degrade PET in a form of ethylene glycol and terephthalate, and may be used for a composition for degrading PET. Specifically, the composition for degrading PET may contain a strain for producing the recombinant PETase and/or a strain for producing the recombinant MHETase, and may contain the recombinant PETase and/or recombinant MHETase as produced from the strain. In this connection, the recombinant MHETase is an enzyme degrading MHET as an intermediate degraded product of PET. Thus, the recombinant MHETase alone may not degrade PET. Thus, the composition for degrading the PET contains the recombinant PETase producing strain or the recombinant PETase produced therefrom. Alternatively, preferably, the composition may contain both the recombinant PETase producing strain or the recombinant PETase produced therefrom, and the recombinant MHETase producing strain or the recombinant MHETase produced therefrom. To completely degrade PET, the composition contains both the strains that may produce the recombinant PETase and recombinant MHETase respectively. It is most desirable that the composition contains both the recombinant PETase and recombinant MHETase produced from the strains.

PET may be degraded using the composition for degrading PET. Specifically, the PET degrading method may include contacting the composition for degrading the PET with the PET. The contacting causes the recombinant PETase and recombinant MHETase to react with PET. The reaction condition is 30° C. or higher and 24 hours or longer in terms of a temperature and a reaction time so that the enzyme activity of the recombinant PETase and recombinant MHETase contained in the composition for degrading PET is realized. In particular, the activity of the recombinant enzymes is maintained for a long time even at high temperatures. Thus, it is most preferable to react the enzyme with PET for a reaction time greater than or equal to 72 hours at 40° C. or higher to improve the degrading ability of PET. In this way, PET may be eventually degraded into ethylene glycol and terephthalate.

According to exemplary embodiments of the present invention, the recombinant PETase and recombinant MHETase may be produced at a high yield. The recombinant PETase and recombinant MHETase have long-term enzyme activity at high temperatures. Thus, the complete biodegradation of large quantities of PET may be achieved using these recombinant enzymes.

DETAILED DESCRIPTION

Hereinafter, the present invention will be described in more detail with reference to the accompanying drawings.

However, these descriptions are presented by way of example only to assist in understanding the present invention. The scope of the present invention is not limited to these exemplary descriptions.

Experimental Example 1. Preparation of Recombinant IsPETase Expression Vector

Figure 1:
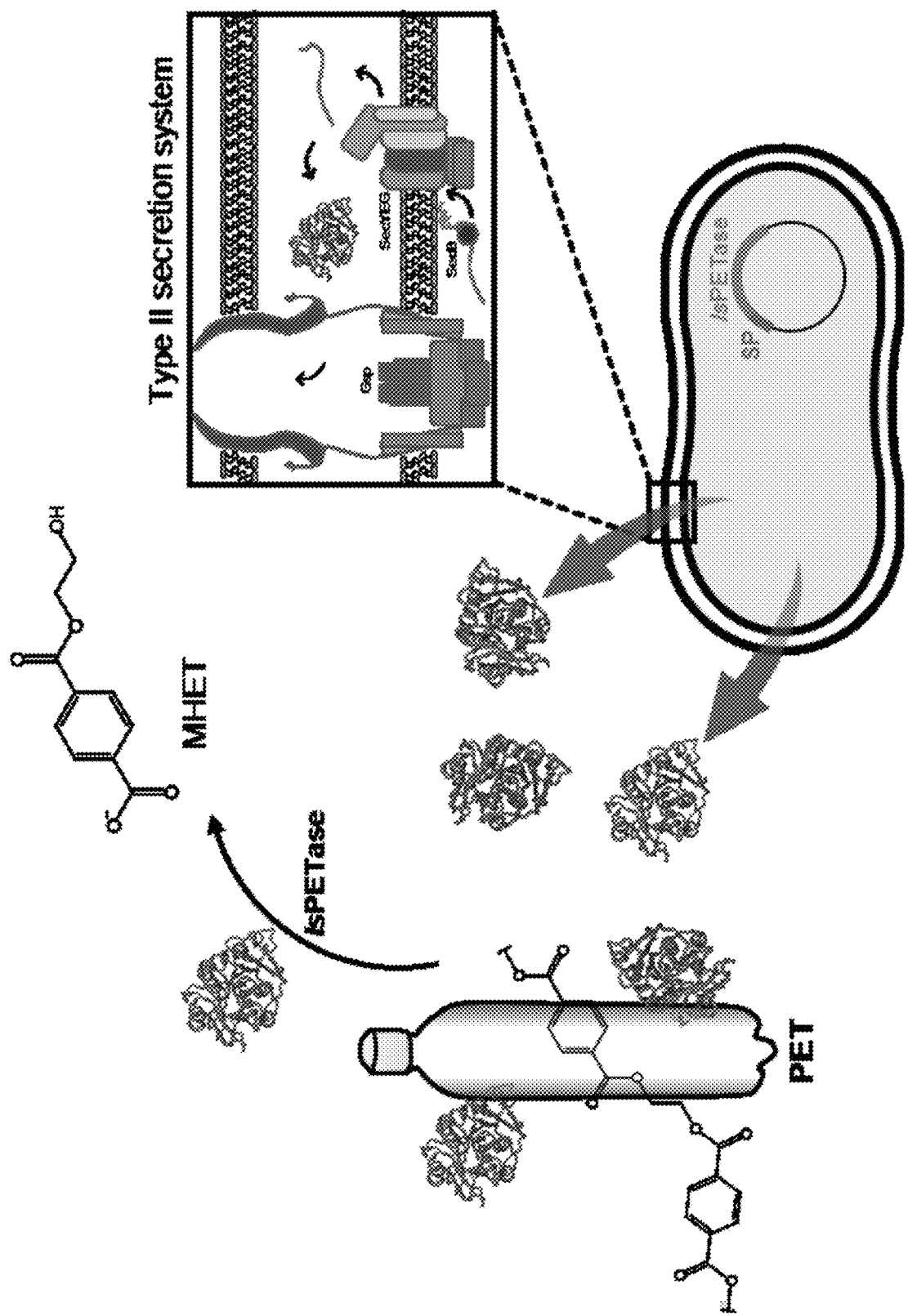
FIG. 1 is a schematic view of a recombinant IsPETase prepared according to the present invention. An expression vector containing a signal peptide (SP) and a poly polynucleotide encoding IsPETase is transformed into *E. coli*. The transformant secretes recombinant IsPETase extracellularly through a Gsp-Sec secretion system (Type-II secretion system Gsp and Sec machinery) of an endomembrane. The secreted IsPETase degrades PET into the monomeric MHET form.

As shown in FIG. 1, an expression vector containing a polynucleotide encoding IsPETase and a signal peptide was prepared.

Figure 2:
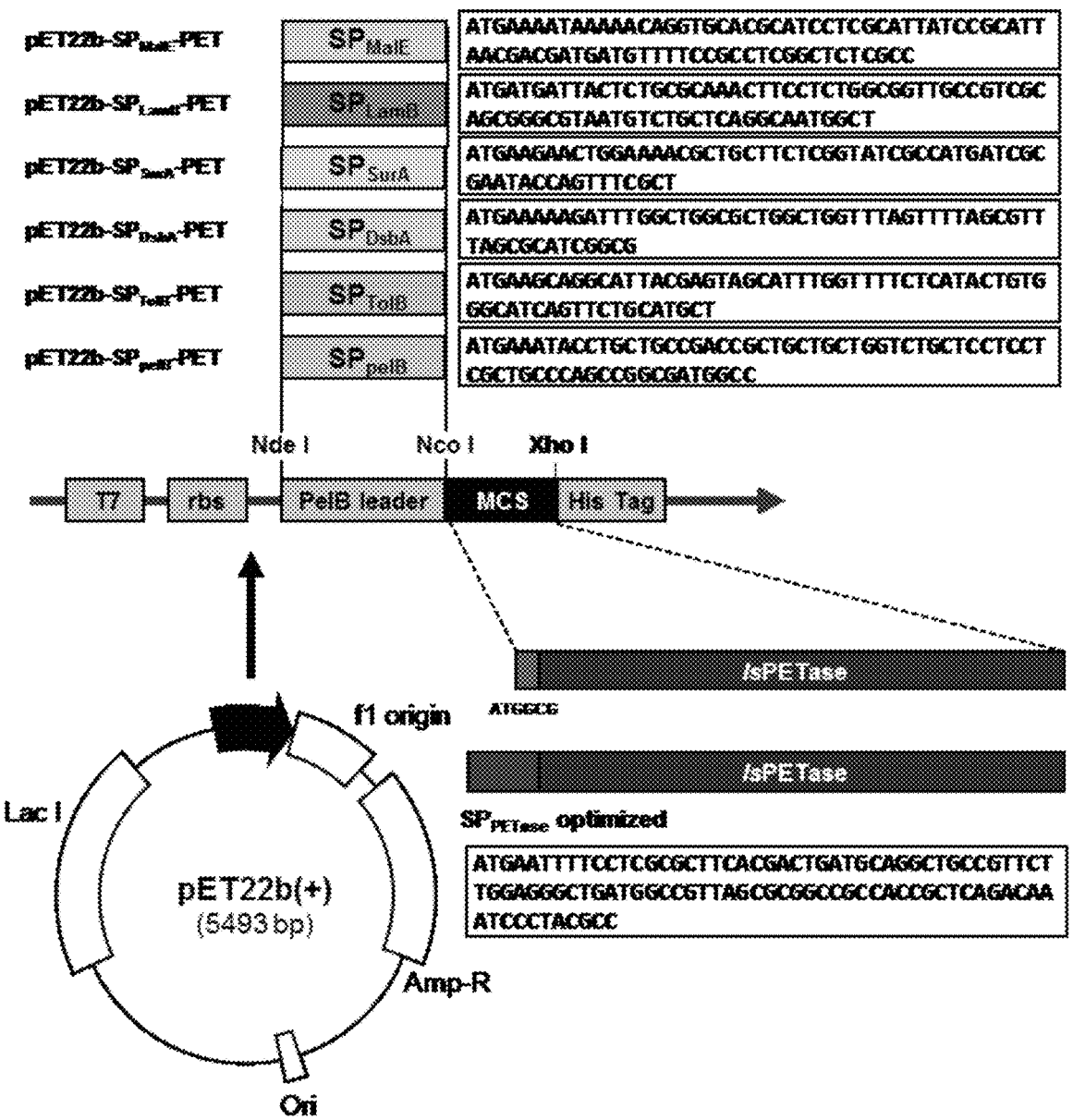
FIG. 2 shows a result of Experimental Example 1 of the present invention. The result shows a structure of the vector expressing IsPETase and a nucleotide sequence of the signal peptide as used ($SP_{MalE}$: SEQ ID NO:43; $SP_{LamB}$: SEQ ID NO:44; $SP_{SurA}$: SEQ ID NO:45; $SP_{DsbA}$: SEQ ID NO:46; $SP_{TolB}$: SEQ ID NO:47; $SP_{pelB}$: SEQ ID NO:48; SP PETase: SEQ ID NO:49).

First, five types of Sec-dependent signal peptides expressed in *E. coli* (maltose/maltodextrin binding periplasmic protein; $SP_{MalE}$ 1 maltoporin; $SP_{LamB}$, periplasmic molecular chaperone SurA; $SP_{SurA}$, thiol:disulfide interchange protein DsbA; $SP_{DsbA}$, and Tol-Pal system protein TolB; $SP_{TolB}$) were used to prepare the expression vector. As shown in FIG. 2, pET22b (+) vector (Novagen/Merck) without a leader sequence was used as the expression vector. Codon optimized oligonucleotides expressing IsPETase were synthesized. At this time, nucleotide CG was further added to an N-terminus of the oligonucleotide to prevent occurrence of a frame shift due to a restriction enzyme Nco I (CCATGG) in the vector. Then, a PelB leader sequence in the vector was removed using restriction enzymes Nde I and Nco I. 5 kinds of Sec-dependent signal peptides, that is, $SP_{malE}$, $SP_{LamB}$, $SP_{SurA}$, $SP_{DsbA}$, and $SP_{TolB}$ which were amplified by polymerase chain reaction (PCR) were inserted into a site in which the PelB leader sequence is removed. Finally, expression vectors pET22b-$SP_{pelB}$:IsPETase, pET22b-$SP_{MalE}$:IsPETase, pET22b-$SP_{LamB}$:IsPETase, pET22b-$SP_{surA}$:IsPETase, pET22b-$SP_{DsbA}$:IsPETase, and pET22b-$SP_{TolB}$:IsPETase were prepared.

An expression vector pET21a-PET (free of signal peptide) containing only a codon-optimized oligonucleotide expressing IsPETase was prepared, as a negative control, using a pET21a vector (Novagen/Merck) without the PelB leader sequence.

In this connection, primers as used are listed in Table 1 below.

TABLE 1

| Primer | Sequence (5' > 3')* |
|---|---|
| IsPETase_F (SEQ ID NO: 13) | GCGC<u>CCATGG</u>CGCGCGGTCCGAATCCGACAGCCG |
| IsPETase_R (SEQ ID NO: 14) | GCGC<u>CTCGAG</u>GCTGCAATTCGCTGTACGAAAATC |
| $SP_{malE}$_F (SEQ ID NO: 15) | GCGC<u>CATATG</u>AAAATAAAAACAGGTGCACGCATC |
| $SP_{malE}$_R (SEQ ID NO: 16) | GCGC<u>CCATGG</u>CGAGAGCCGAGGCGGAAAACATCA |
| $SP_{LamB}$_F (SEQ ID NO: 17) | GCGC<u>CATATG</u>ATGATTACTCTGCGCAAACTTCCT |
| $SP_{LamB}$_R (SEQ ID NO: 18) | GCGC<u>CCATGG</u>CCATTGCCTGAGCAGACATTACGC |
| $SP_{SurA}$_F (SEQ ID NO: 19) | GCGC<u>CATATG</u>AAGAACTGGAAAACGCTGCTTCTC |
| $SP_{SurA}$_R (SEQ ID NO: 20) | GCGC<u>CCATGG</u>CGAAACTGGTATTCGCGATCATGG |
| $SP_{DsbA}$_F (SEQ ID NO: 21) | GCGC<u>CATATG</u>AAAAAGATTTGGCTGGCGCTGGCT |
| $SP_{DsbA}$_R (SEQ ID NO: 22) | GCGC<u>CCATGG</u>CCGATGCGCTAAACGCTAAAACTA |
| $SP_{TolB}$_F (SEQ ID NO: 23) | GCGC<u>CATATG</u>AAGCAGGCATTACGAGTAGCATTT |
| $SP_{TolB}$_R (SEQ ID NO: 24) | GCGC<u>CCATGG</u>CATGCAGAACTGATGCCCACAGTA |

*Restriction enzyme cut sites are underlined

Experimental Example 2. Expression and Purification of Recombinant IsPETase

Each of the seven recombinant IsPETase expression vectors prepared in Experimental Example 1 was transformed into *E. coli* BL21 (DE3)-T1R cells to obtain each of transformants. Each transformant was inoculated in 1 L of LB medium containing 200 mg·$L^{-1}$ of ampicillin and was incubated therein at 37° C. To induce protein expression, 0.1 mM IPTG was added to the culture medium when the OD600 nm reached 0.6, followed by further incubation at 130 rpm for 24 hours at 18° C. in a shaking incubator. Thereafter, the culture medium was centrifuged at 4° C. and at 6,000×g for 30 minutes to recover a supernatant. 100 mL of the supernatant was concentrated 50-fold at 4° C. using a centrifugal filter (Amicon® Ultra-15 10K centrifugal filter, Millipore) to obtain 2 mL of concentrate. The concentrate was analyzed using electrophoresis (SDS-PAGE) to determine the expression level of the protein. The result is shown in (A) of FIG. 3.

Figure 3:
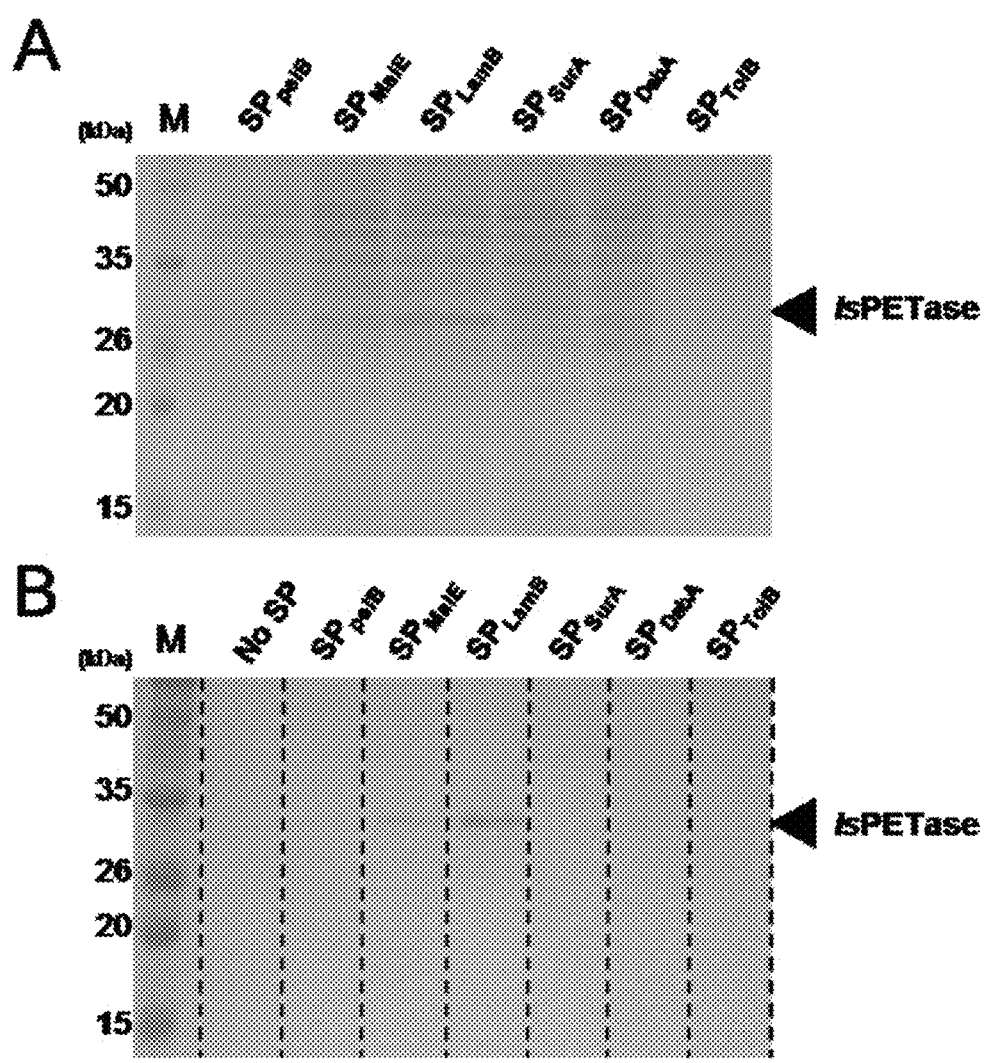
FIG. 3 shows a result for Experimental Example 2 of the present invention. (A) is a photograph identified by electrophoresis (SDS-PAGE) after concentrating a culture medium containing the recombinant IsPETase. In this connection, M is a protein molecular weight marker. (B) is a photograph identified by electrophoresis (SDS-PAGE) after purification of the recombinant IsPETase from a culture medium containing the recombinant IsPETase. In this connection, M is a protein molecular weight marker.

As shown in (A) of FIG. 3, a protein band of about kDa was identified in the expression vectors pET22b-SP$_{MalE}$:IsPETase and pET22b-SP$_{LamB}$:IsPETase. This band is assumed to be IsPETase (28 kDa). It was found that each expression vector expresses the recombinant IsPETase. However, a protein band was not identified in the expression vectors pET22b-SP$_{pelB}$:IsPETase, pET22b-SP$_{surA}$:IsPETase, pET22b-SP$_{DsbA}$:IsPETase, and pET22b-SP$_{TolB}$:IsPETase.

To observe the expression of recombinant IsPETase in more detail, the protein was purified using affinity chromatography.

First, the concentrate was diluted in a cold buffer A (40 mM Tris-HCl, pH 8.0) and then 50 mL of the diluent was loaded onto a Ni-NTA agarose column (Qiagen). Thereafter, a buffer A containing 9 mM imidazole was loaded on the column, and then 15 mL of a buffer A containing 300 mM imidazole was loaded on the column again to elute the protein. The eluate was concentrated using a centrifugal filter to obtain 2 mL of concentrate. The concentrate was analyzed using electrophoresis (SDS-PAGE) to determine the expression level of the purified protein. The result is shown in (B) of FIG. 3. Further, the purified protein was quantified using a BioTek™ Epoch microplate spectrophotometer and a Gen5™ microplate data analysis software. An absorption coefficient value of the protein was obtained using ExPASy server's ProtParam tool.

As shown in (B) of FIG. 3, a protein band of about 29 kDa was identified in the expression vectors pET22b-SP$_{malE}$:IsPETase, and pET22b-SP$_{LamB}$:IsPETase. However, a protein band was not identified in the expression vectors pET21a:IsPETase (No SP), pET22b-SP$_{pelB}$:IsPETase, pET22b-SP$_{SurA}$:IsPETase, pET22b-SP$_{DsbA}$:IsPETase, and pET22b-SP$_{TolB}$:IsPETase. These results were the same as shown in (A) of FIG. 3, which measured the expression level of the protein without purification. In particular, the expression protein level of pET22b-SP$_{LamB}$:IsPETase was 6.2 mg/L, which was identified to be a larger amount compared to 3.0 mg/L of pET22b-SP$_{malE}$:IsPETase.

As a result, the expression vectors pET22b-SP$_{MalE}$:IsPETase and pET22b-SP$_{LamB}$:IsPETase containing maltose transportation-related peptides among the Sec-dependent signal peptides secrete a large amount of recombinant IsPETase extracellularly. To the contrary, the expression vectors pET22b-SP$_{DsbA}$:IsPETase and pET22b-SP$_{TolB}$:IsPETase containing co-translational SRP-route-related peptides did not secrete the recombinant IsPETase. Thus, it was found that the recombinant IsPETase performs inner membrane translocation through the Sec-dependent pathway.

Experimental Example 3. PET Degrading Ability Test of Recombinant IsPETase

In order to measure the enzyme activity of recombinant IsPETase, PET degrading ability test was performed. PET is degraded to MHET by IsPETase. MHET is degraded to ethylene glycol and terephthalate by IsMHETase.

A PET film (UBIGEO, Korea) was prepared as a substrate in a disc shape (diameter 6 mm). IsPETase employed a recombinant protein purified from the expression vector pET22b-SP$_{LamB}$:IsPETase of Experimental Example 2.

First, the PET film was placed in 300 μL of 50 mM glycine/NaOH (pH 9) containing 200 nM IsPETase and reacted at 30° C. for 24 hours or 72 hours. We removed the PET film and heated the remaining reaction solution at 85° C. for 15 minutes to complete the enzyme reaction. The supernatant was obtained by centrifugation thereof at 13,500×g for 10 minutes. The supernatant was then subjected to liquid chromatography (CMB-20A HPLC, Shimadzu) (using UV/Vis detector (SPD-20A) and C18 column (SunFire™, 5 μm, 4.6×250 mm)). A buffer A as the mobile phase used distilled water containing 0.1% formic acid. A buffer B as a mobile phase used acetonitrile. A flow rate was fixed at 0.8 mL·min$^{-1}$ In the measurement, the buffer B as the mobile phase gradually increased from 1% buffer B to 5% buffer B which was used for 5 minutes and then 100% buffer B was used for 10 minutes. MHET and terephthalate were measured at 260 nm in absorbance using the final mobile phase. The result is shown in FIG. 4.

Figure 4:
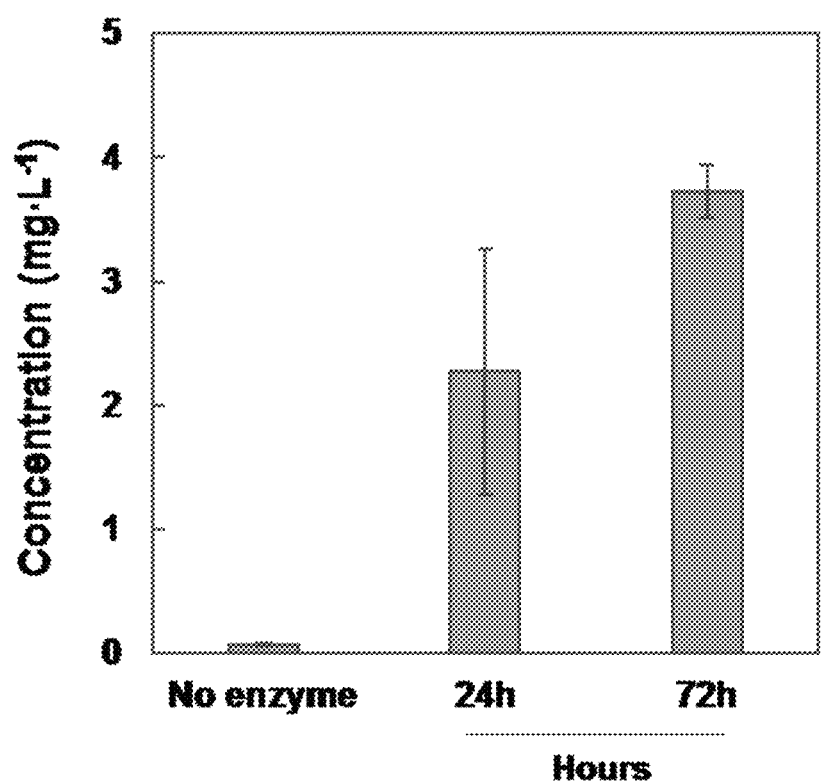
FIG. 4 shows a result of Experimental Example 3 of the present invention and shows a graph of a time-dependent enzyme activity of the recombinant IsPETase. In this connection, "No enzyme" refers to a case without treatment with the recombinant IsPETase.

As shown in FIG. 4, recombinant IsPETase was identified as degrading PET film to produce MHET and terephthalate. At this time, when the recombinant IsPETase and PET film were reacted with each other for 24 hours and 72 hours, the concentrations of MHET and terephthalate were 2.3 mg·L$^{-1}$ and 3.7 mg·L$^{-1}$, respectively. A PET degrading ability of recombinant IsPETase increases over time and could last for up to 72 hours.

Experimental Example 4. Preparation of Recombinant IsMHETase Expression Vector

An expression vector containing a polynucleotide encoding MHETase and a signal peptide was prepared.

In the same manner as Experimental Example 1, five types of signal peptides and pET22b (+) vector were used to prepare following expression vectors: pET22b-SP$_{pelB}$:IsMHETase, pET22b-SP$_{MalE}$:IsMHETase, pET22b-SP$_{LamB}$:IsMHETase, pET22b-SP$_{SurA}$:IsMHETase, and pET22b-SP$_{DsbA}$:IsMHETase, pET22b-SP$_{TolB}$:IsMHETase.

In this connection, signal peptide-related primers as used are shown in Table 1 above. IsMHETase-related primers are shown in Table 2 below.

TABLE 2

| Primers | Sequence (5' > 3')* |
|---|---|
| IsMHETase_F (SEQ ID NO: 25) | GCGC<u>CCATGG</u>CGTGTGCTGGCGGTGGGTCCACGC |
| IsMHETase_R (SEQ ID NO: 26) | GCGCG<u>CTCGAG</u>GGGAGGAGCCGCGCAGGCG |

*Restriction enzyme cut sites are underlined

Experimental Example 5. Expression and Purification of Recombinant IsMHETase

In the same manner as in Experimental Example 2, we used each of the seven recombinant IsMHETase expression vectors prepared in the Experimental Example 4 to obtain each culture medium (C) containing each recombinant IsMHETase.

The culture medium was centrifuged at 4° C. and 6,000×g for 30 minutes to separate a precipitate (P) and a supernatant (S). The supernatant was diluted in a cold buffer A (40 mM Tris-HCl, pH 8.0) and then 50 mL of the diluent was loaded onto a Ni-NTA agarose column (Qiagen) to obtain eluent (F) passing through the column. Thereafter, we loaded a buffer A on the column to obtain eluate (L). Again, a buffer A containing 9 mM imidazole was loaded on the column to obtain eluate (3). Finally, 15 mL of buffer A containing 300 mM imidazole was loaded onto the column twice to obtain an eluate containing protein. The eluate was concentrated by a centrifugal filter to obtain 2 mL of each of concentrates (E1, E2). In order to measure the expression level of the protein, the culture medium (C), the precipitate (P), the supernatant (S), the eluate (F), the eluate (L), the eluate (3), and the concentrates (E1, E2) were analyzed using electrophoresis (SDS-PAGE). The result is shown in FIG. 5.

Figure 5:
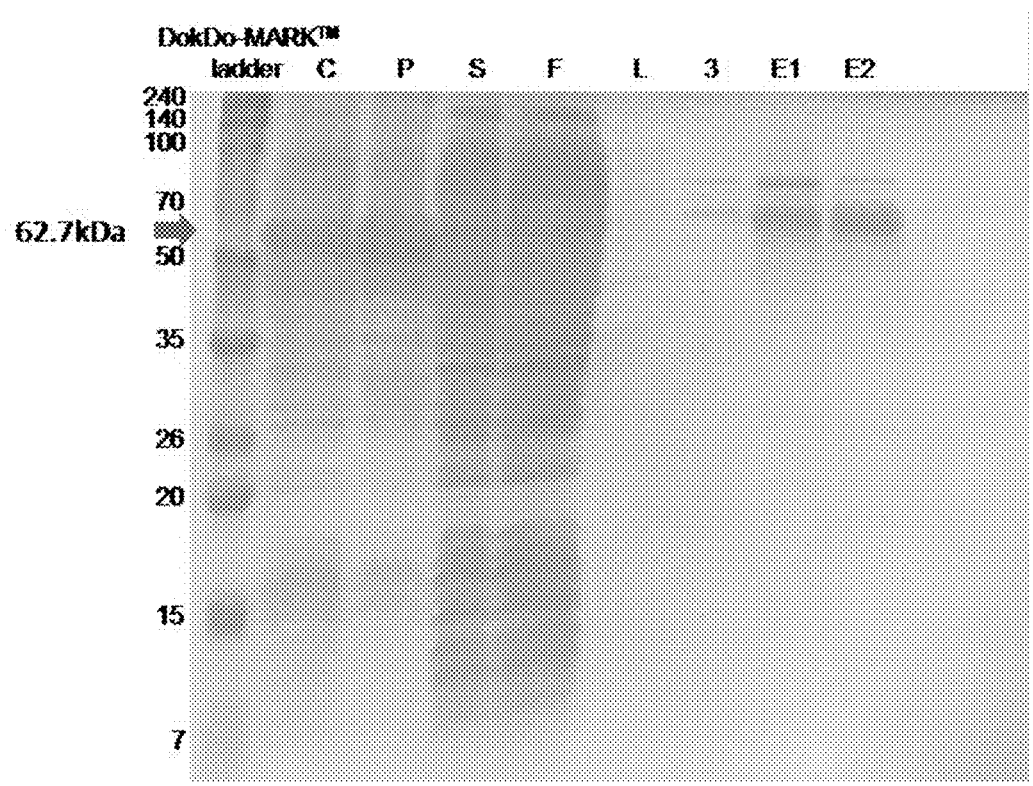
FIG. 5 shows a result for Experimental Example 5 of the present invention. The result shows a photograph identified by electrophoresis (SDS-PAGE) of a culture medium (C) containing recombinant IsMHETase, and a precipitate (P), supernatant (S), eluate (F, L, 3) and concentrate (E1, E2) as separated therefrom. In this connection, Ladder is a protein molecular weight marker.

As shown in FIG. 5, a protein band of about 63 kDa was identified in the culture medium (C), supernatant (S) and concentrates (E1, E2) of the expression vector pET22b-$SP_{LamB}$:IsMHETase. This band could be assumed to be IsMHETase (62.7 kDa). However, no protein bands were identified in the expression vectors pET22b-$SP_{pelB}$:IsMHETase, pET22b-$SP_{MalE}$:IsMHETase, pET22b-$SP_{SurA}$:IsMHETase, pET22b-$SP_{DsbA}$:IsMHETase, and pET22b-$SP_{TolB}$:IsMHETase.

Therefore, like the recombinant IsPETase of Experimental Example 2, recombinant IsMHETase performs inner membrane translocation through the Sec-dependent pathway.

Experimental Example 6. Regulation of Expression of Recombinant IsMHETase Using Chaperone To enhance the extracellular expression of recombinant IsPETase, expression of IsMHETase was regulated using various chaperones. In this experimental example, five types of chaperones (FkpA, DsbA, DsbC, SPaseI, and SecB) were used.

First, a pET30a vector (Novagen/Merck) or a pCDF-duet-1 vector (Novagen/Merck) was used as the chaperone expression vector. Codon optimized oligonucleotides expressing chaperone were synthesized. Finally, expression vectors pET30a:FkpA, pET30a:DsbA, pET30a:SPaseI, pCDFduet-1:SecB, pCDFduet-1:DsbC, and pCDFduet-1:SPaseI+SecB were prepared.

In this connection, primers as used are shown in Table 3 below.

The six recombinant chaperone expression vectors together with the recombinant pET22b-$SP_{LamB}$:IsMHETase expression vector prepared in Experimental Example 4 were transformed into *E. coli* BL21 (DE3)-T1R cells to obtain transformants. In the same manner as in Experimental Example 2, a culture medium (C) containing a recombinant IsMHETase folded by chaperone was obtained.

The culture medium was centrifuged at 4° C. and 6,000×g for 30 minutes to separate a precipitate (P) and a supernatant (S). The supernatant was diluted in a cold buffer A (40 mM Tris-HCl, pH 8.0) and then 50 mL of the diluent was loaded onto a Ni-NTA agarose column (Qiagen) to obtain eluent (F) passing through the column. Thereafter, we loaded a buffer A on the column to obtain eluate (L). Again, a buffer A containing 9 mM imidazole was loaded on the column to obtain eluate (3). Finally, 15 mL of buffer A containing 300 mM imidazole was loaded onto the column twice to obtain an eluate containing protein. The eluate was concentrated by a centrifugal filter to obtain 2 mL of concentrate (E). In order to measure the expression level of the protein, the culture medium (C), the precipitate (P), the supernatant (S), the eluate (F), the eluate (L), the eluate (3), and the concentrate (E) were analyzed using electrophoresis (SDS-PAGE). The result is shown in FIG. 6.

Figure 6:
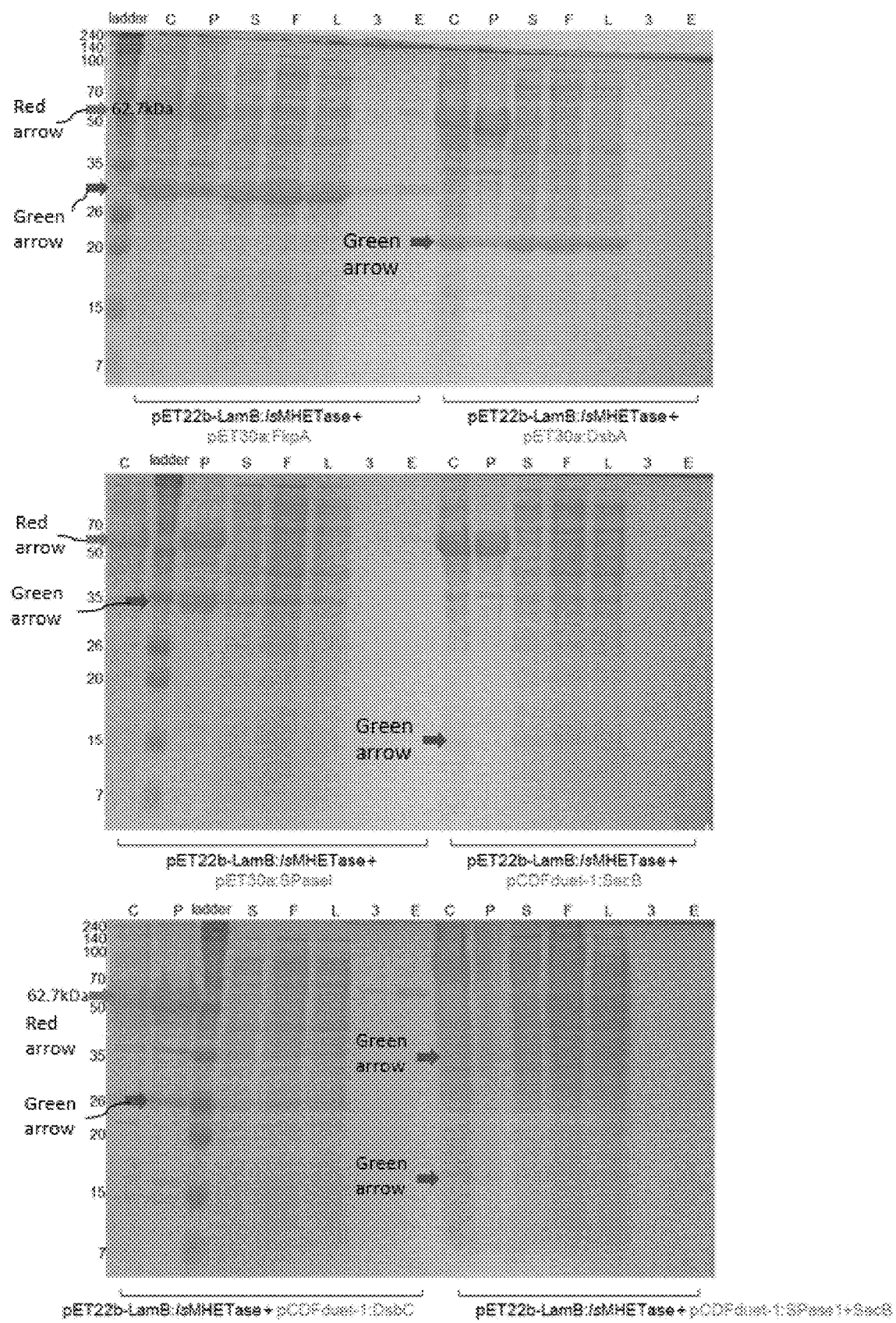
FIG. 6 shows a result of Experimental Example 6 of the present invention. The result shows a photograph identified by electrophoresis (SDS-PAGE) of a culture medium (C) containing recombinant IsMHETase folded by chaperone, and a precipitate (P), supernatant (S), and eluate (F, L, 3), and concentrate (E) as separated therefrom. In this connection, Ladder is a protein molecular weight marker. A red arrow denotes an IsMHETase band. A green arrow denotes a chaperone band.

As shown in FIG. 6, the concentration (E) containing recombinant IsMHETase expressed together with chaperone DsbC exhibited a twofold thicker protein band compared to the recombinant IsMHETase expressed together with other chaperones. Thus, it could be identified that recombinant IsMHETase has the best extracellular expression because the protein structure thereof is stabilized by the chaperone DsbC.

Experimental Example 7. PET Degrading Ability of Recombinant IsMHETase

In order to measure the enzyme activity of recombinant IsMHETase, PET degrading ability test was performed. PET is degraded to MHET by IsPETase. MHET is degraded to ethylene glycol and terephthalate by MHETase.

A PET film (UBIGEO, Korea) was prepared as a substrate in a disc shape (diameter 6 mm). IsPETase employed IsPETase$^{WT}$, and IsPETase$^{S121E/D186H/R280A}$. IsMHETase

TABLE 3

| Primers | Sequence (5′ > 3′)* |
|---|---|
| FkpA_F (SEQ ID NO: 27) | GCGCCATATGAAATCACTGTTTAAAGTAACGCTG |
| FkpA_R (SEQ ID NO: 28) | GCGCCTCGAGTTATTTTTTAGCAGAATCTGCGGC |
| DsbC_F (SEQ ID NO: 29) | GCGCCCATGGAGAAAGGTTTTATGTTGTTTACTT |
| DsbC_R (SEQ ID NO: 30) | GCGCGCGGCCGCTTATTTACCGCTGGTCATTTTT |
| DsbA_F (SEQ ID NO: 31) | GCGCCATATGAAAAAGATTTGGCTGGCGCTGGCT |
| DsbA_R (SEQ ID NO: 32) | GCGCCTCGAGTTATTTTTTCTCGGACAGATATTT |
| SecB_F (SEQ ID NO: 33) | GCGCCCATGGCAGAACAAAACAACACTGAAATGA |
| SecB_R (SEQ ID NO: 34) | GCGCGCGGCCGCTCAGGCATCCTGATGTTCTTCA |
| SPaseI_F (SEQ ID NO: 35) | GCGCCATATGGCGAATATGTTTGCCCTGATTCTG |
| SPaseI_R (SEQ ID NO: 36) | GCGCCTCGAGTTAATGGATGCCGCCAATGCGACT |

*Restriction enzymes are underlined employed a recombinant protein purified from the expression vector pET22b-SP$_{LamB}$:IsMHETase as prepared in Experimental Example 5.

The IsPETase$^{WT}$ is a wild type IsPETase expressed from natural *Ideonella sakaiensis*. IsPETase$_{S121E/D186H/R280A}$ is recombinant IsPETase in which 121th serine, 186th aspartate and 280th arginine among the amino acid sequences of the wild type IsPETase were substituted with glutamate, histidine and alanine, respectively. IsPETase$^{S121E/D186H/R280A}$ was prepared in the same manner as Experimental Examples 1 and 2. In this connection, primers as used are shown in Table 4 below.

TABLE 4

| Primers | Sequence (5' > 3')* |
|---|---|
| IsPETase_S121E_F (SEQ ID NO: 37) | ACGTTAGACCAGCCAGAAAGTCGGAGTTCGCAA |
| IsPETase_S121E_R (SEQ ID NO: 38) | TTGCGAACTCCGACTTTCTGGCTGGTCTAACGT |
| IsPETase_D186H_F (SEQ ID NO: 39) | CCTCAAGCACCATGGCATTCTTCGACAAATTT |
| IsPETase_D186H_R (SEQ ID NO: 40) | AAAATTTGTCGAAGAATGCCATGGTGCTTGAGG |
| IsPETase_R280A_F (SEQ ID NO: 41) | AACCCGAATAGCACCAGAGTGTCTGATTTTCGT |
| IsPETase_R280A_R (SEQ ID NO: 42) | ACGAAAATCAGACACTCTGGTGCTATTCGGGT |

*Substituted nucleotide sequences are underlined

In the same manner as Experimental Example 3, a PET film, recombinant IsPETase and recombinant IsMHETase were reacted with each other at 30° C. or 40° C. for 24 hours or 72 hours to obtain supernatant. The supernatant was used to measure MHET and terephthalate. The result is shown in FIG. 7.

Figure 7:
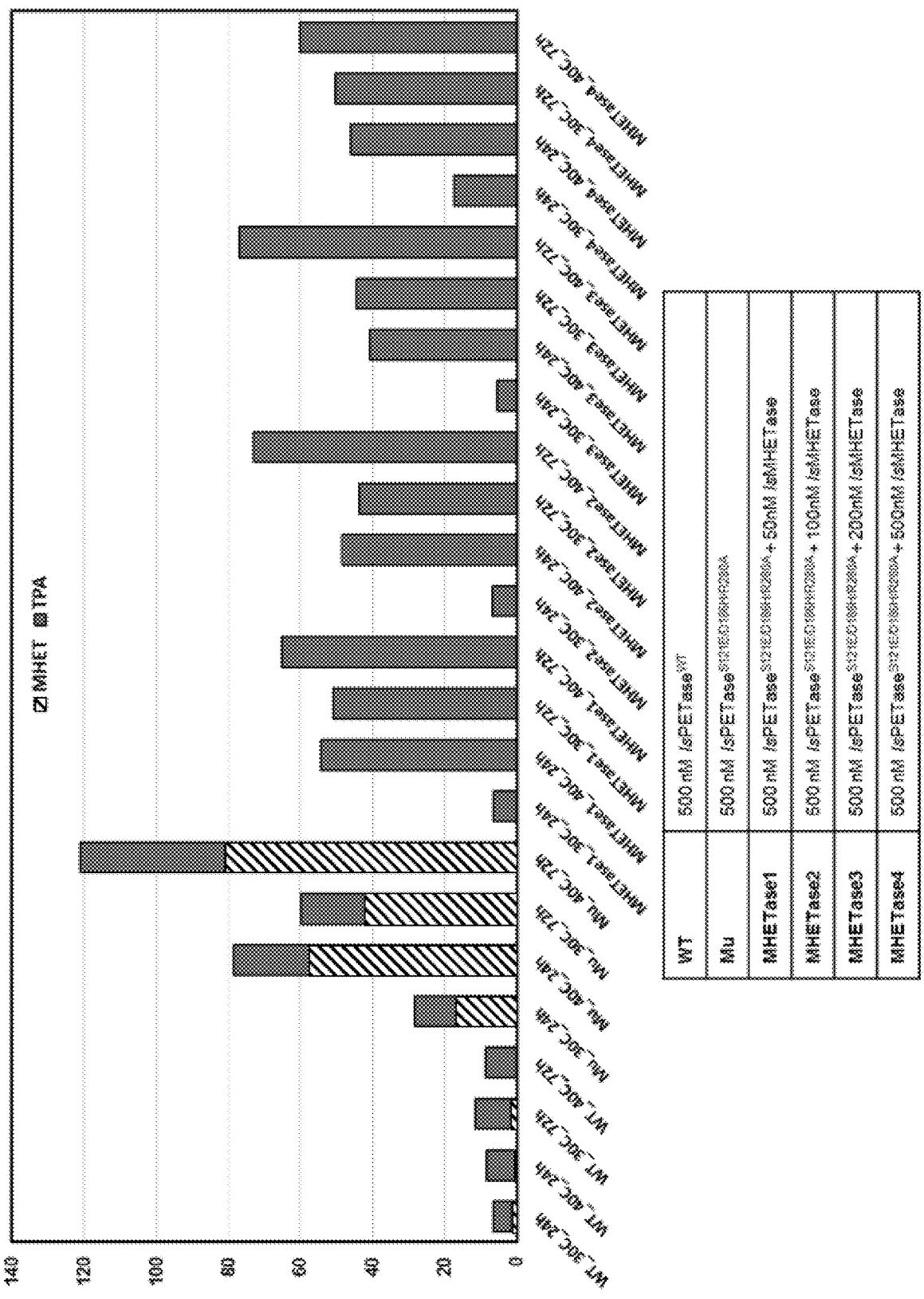
FIG. 7 shows a result of Experimental Example 7 of the present invention. This shows a graph of measurements of the recombinant IsPETase and the recombinant IsMHETase, and enzyme activity thereof based on temperature, time and concentration.

As shown in FIG. 7, it was identified that when the PET film was treated with both of the recombinant IsPETase and recombinant IsMHETase, the PET film was completely degraded to produce only terephthalate (TPA). In this case, it was identified that the higher the reaction temperature, the longer the reaction time, the more terephthalate is produced. Further, it was identified that when the concentrations of recombinant IsMHETase were 50 and 100 nM, they more efficiently degrade the PET than at high concentrations (200, 500 nM).

In order to observe the activity of recombinant IsMHETase in more detail, affinity chromatography was used to measure MHET and terephthalate in the supernatant. The result is shown in FIG. 8.

Figure 8:
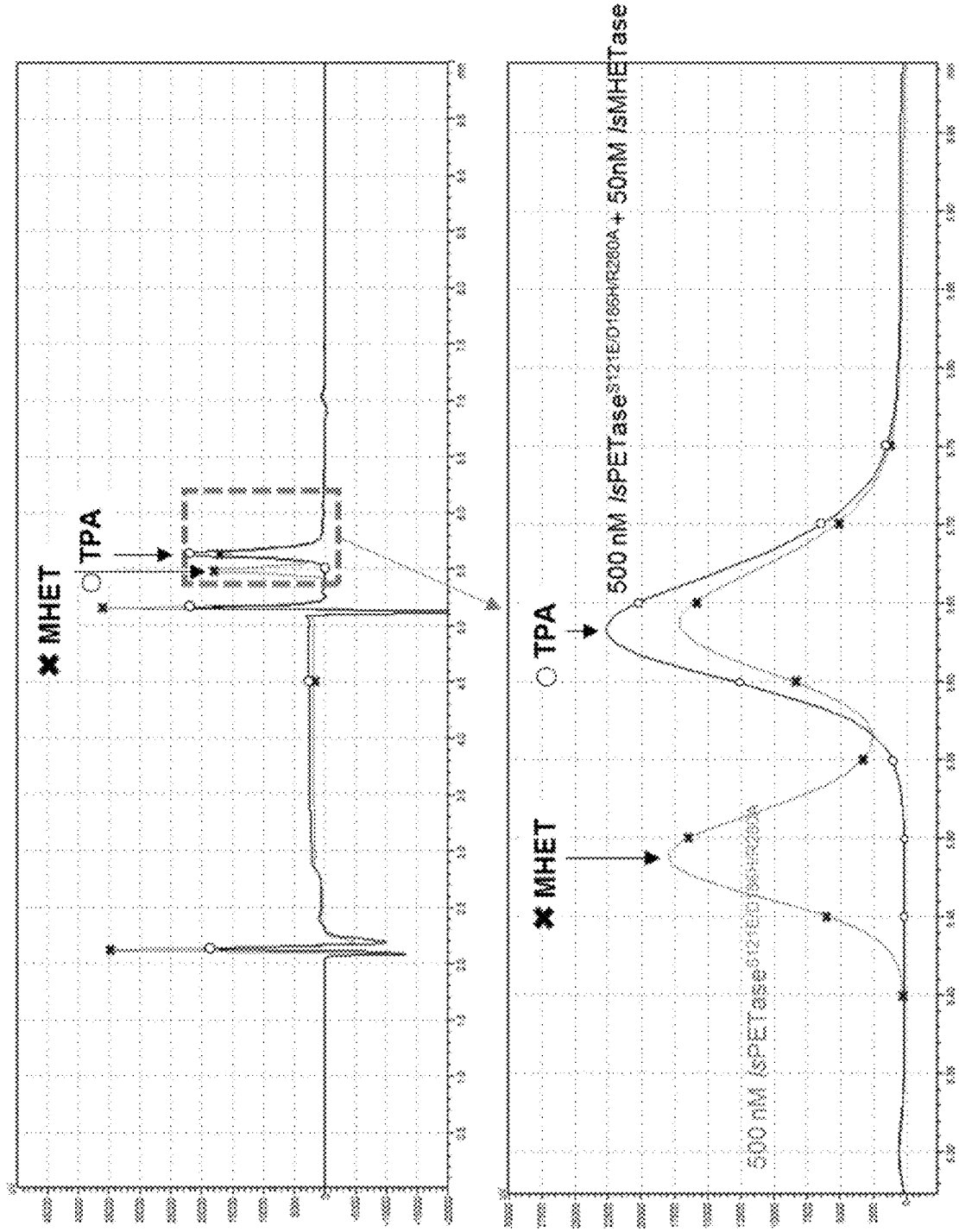
FIG. 8 shows an experimental result of Experimental Example 7 of the present invention. This shows a graph of measurements of the recombinant IsPETase, and MHET and terephthalate (TPA) produced by the recombinant IsPETase and the recombinant IsMHETase.

As shown in FIG. 8, when the PET was treated with both of recombinant IsPETase$^{S121E/D186H/R280A}$ and the recombinant IsMHETase, MHET is completely degraded, compared to the treatment of the PET with only the recombinant IsPETase$^{S121E/D186H/R280A}$. Thus, only terephthalate (TPA) was produced. An amount of terephthalate as produced was identified to be larger.

As a result, the present invention may provide the producing strains that express the recombinant enzymes extracellularly using the recombinant IsPETase and recombinant IsMHETase expression vectors. The recombinant enzymes IsPETase and IsMHETase expressed from the strains were used to achieve the complete degrading of PET.

The present invention has been described based on the preferred embodiments. Those of ordinary skill in the technical field to which the present invention belongs may understand that the present invention may be implemented in a modified form without departing from the essential characteristics of the present invention. Therefore, the disclosed embodiments should be considered in descriptive sense only and not for purposes of limitation. The scope of the present invention is indicated in the claims, not the foregoing description. All modifications within the equivalent scope to the claims shall be construed as included in the present invention.

What is claimed is:

1. A recombinant PETase expression vector containing:

a polynucleotide encoding a signal peptide; and a polynucleotide encoding a poly(ethylene terephthalate) hydrolase (PETase) linked to a C-terminus of the polynucleotide encoding a signal peptide, wherein the PETase consists of SEQ ID NO: 6.

2. The recombinant PETase expression vector of claim 1, wherein the signal peptide consists of SEQ ID NO: 1 or SEQ ID NO: 2.

3. The recombinant PETase expression vector of claim 1, wherein the PETase is derived from *Ideonella sakaiensis*.

4. A recombinant PETase producing strain containing the expression vector of claim 1.

* * * * *